United States Patent
Lee et al.

(10) Patent No.: US 10,906,969 B2
(45) Date of Patent: Feb. 2, 2021

(54) LOCAL ORBITAL THERAPY FOR THYROID EYE DISEASE

(71) Applicants: Massachusetts Eye and Ear Infirmary, Boston, MA (US); Schepens Eye Research Institute, Boston, MA (US)

(72) Inventors: N. Grace Lee, Boston, MA (US); Leo Kim, Boston, MA (US); Patricia A. D'Amore, Boston, MA (US); James A. Stefater, Boston, MA (US)

(73) Assignees: Massachusetts Eye and Ear Infirmary, Boston, MA (US); The Schepens Eye Research Institute, Inc., Boston, MA (US)

( * ) Notice: Subject to any disclaimer, the term of this patent is extended or adjusted under 35 U.S.C. 154(b) by 24 days.

(21) Appl. No.: 16/307,411

(22) PCT Filed: Jun. 8, 2017

(86) PCT No.: PCT/US2017/036517
§ 371 (c)(1),
(2) Date: Dec. 5, 2018

(87) PCT Pub. No.: WO2017/218284
PCT Pub. Date: Dec. 21, 2017

(65) Prior Publication Data
US 2019/0276529 A1 Sep. 12, 2019

Related U.S. Application Data

(60) Provisional application No. 62/349,273, filed on Jun. 13, 2016.

(51) Int. Cl.
| | |
|---|---|
| A61K 39/395 | (2006.01) |
| C07K 16/22 | (2006.01) |
| C07K 16/20 | (2006.01) |
| A61K 38/47 | (2006.01) |
| C07K 14/475 | (2006.01) |
| C07K 14/71 | (2006.01) |
| C07K 16/28 | (2006.01) |
| A61K 9/00 | (2006.01) |
| A61K 9/08 | (2006.01) |
| A61K 38/17 | (2006.01) |
| A61K 38/00 | (2006.01) |
| A61K 39/00 | (2006.01) |

(52) U.S. Cl.
CPC ............ C07K 16/22 (2013.01); A61K 9/0048 (2013.01); A61K 9/08 (2013.01); A61K 38/17 (2013.01); A61K 38/47 (2013.01); A61K 39/3955 (2013.01); C07K 14/475 (2013.01); C07K 14/71 (2013.01); C07K 16/2803 (2013.01); C12Y 302/01035 (2013.01); A61K 38/00 (2013.01); A61K 2039/505 (2013.01); A61K 2039/507 (2013.01); C07K 2317/24 (2013.01); C07K 2319/30 (2013.01)

(58) Field of Classification Search
None
See application file for complete search history.

(56) References Cited

U.S. PATENT DOCUMENTS

2008/0057028 A1   3/2008   Alitalo et al.

FOREIGN PATENT DOCUMENTS

| WO | WO 2006/039336 | 4/2006 |
| WO | WO 2008/048770 | 4/2008 |

OTHER PUBLICATIONS

Achen et al., "Vascular endothelial growth factor D (VEGF-D) is a ligand for the tyrosine kinases VEGF receptor 2 (Flk1) and VEGF receptor 3 (Flt4)," PNAS, 1998, 95:548-553.
Alasil et al., "Intravitreal Bevacizumab in the treatment of neovascular glaucoma secondary to central retinal vein occlusion: a case report," Biomed Central Cases Journal, Oct. 2009, 2: 1-4.
Balm, "Graves' ophthalmopathy," N Engl J Med, 2010, 362:726-738.
Bielenberg et al., "Semaphorin 3F, a chemorepulsant for endothelial cells, induces a poorly vascularized, encapsulated, nonmetastatic tumor phenotype," J Clin Invest, 2004, 114:1260-1271.
Bock et al., "Bevacizumab as a potent inhibitor of inflammatory corneal angiogenesis and lymphangiogenesis," Invest Ophthalmol Vis Sci, 2007, 48:2545-2552.
Bothun et al., "Update on thyroid eye disease and management," Clin Ophthalmol, 2009; 3: 543-551.
Cursiefen et al., "Time course of angiogenesis and lymphangiogenesis after brief corneal inflammation," Cornea, 2006, 25:443-447.
Detmar and Hirakawa, "The formation of lymphatic vessels and its importance in the setting of malignancy," J Exp Med, 2002, 196:713-718.
Detmar et al., "Increased microvascular density and enhanced leukocyte rolling and adhesion in the skin of VEGF transgenic mice," J Invest Dermatol, 1998, 111:1-6.
Dolman and Rootman, "VISA Classification for Graves orbitopathy," Ophthal Plast Reconstr Surg, 2006, 22(5):319-24.
Fogt et al., "Observation of lymphatic vessels in orbital fat of patients with inflammatory conditions: a form fruste of lymphangiogenesis?," Int J Mol Med, 2004, 13:681-683.
Folkman, "Fundamental concepts of the angiogenic process," Curr Mol Med, 2003, 3:643-651.
Gausas et al., "Identification of human orbital lymphatics," Ophthal Plast Reconstr Surg, 1999, 15:252-259.

(Continued)

*Primary Examiner* — Christine J Saoud
*Assistant Examiner* — Jon M Lockard
(74) *Attorney, Agent, or Firm* — Fish & Richardson P.C.

(57) ABSTRACT

Methods of treating acute thyroid eye disease (TED) by administering a inhibitor, e.g., a VEGF-A inhibitor, e.g., an anti-VEGF antibody, optionally in combination with hyaluronidase, by periorbital or intraorbital injection. Also compositions comprising a VEGF inhibitor and hyaluronidase.

5 Claims, 4 Drawing Sheets

Specification includes a Sequence Listing.

(56) References Cited

OTHER PUBLICATIONS

Gausas, "Advances in applied anatomy of the eyelid and orbit," Curr Opin Ophthalmol, 2004, 15:422-425.

Haiko et al., "Deletion of vascular endothelial growth factor C (VEGF-C) and VEGF-D is not equivalent to VEGF receptor 3 deletion in mouse embryos," Mol Cell Biol, 2008, 28:4843-4850.

Harvey, "The link between lymphatic function and adipose biology," Ann N Y Acad Sci, 2008, 1131:82-88.

Hong and Detmar, "Prox1, master regulator of the lymphatic vasculature phenotype," Cell Tissue Res, 2003, 314:85-92.

Huggenberger et al., "An important role of lymphatic vessel activation in limiting acute inflammation," Blood, 2011, 117:4667-4678.

International Preliminary Report on Patentability in International Application No. PCT/US2017/36517, dated Dec. 18, 2018, 9 pages.

International Search Report and Written Opinion in International Application No. PCT/US2017/36517, dated Sep. 7, 2017, 19 pages.

Kaipainen et al., "Enhanced expression of the tie receptor tyrosine kinase messenger RNA in the vascular endothelium of metastatic melanomas," Cancer Res, 1994, 54:6571-6577.

Karkkainen et al., "Molecular regulation of lymphangiogenesis and targets for tissue oedema," Trends in Molecular Medicine, 2001, 7(1):18-22.

Karkkainen et al., "Vascular endothelial growth factor C is required for sprouting of the first lymphatic vessels from embryonic veins," Nat Immunol, 2004, 5:74-80.

Keck et al., "Vascular permeability factor, an endothelial cell mitogen related to PDGF," Science, 1989, 246:1309-1312.

Killer et al., "Lymphatic capillaries in the meninges of the human optic nerve," J Neuroophthalmol, 1999, 19:222-228.

Macchia et al., "High-dose intravenous corticosteroid therapy for Graves' ophthalmopathy," J Endocrinol Invest, 2001, 24:152-8.

Maheshwari and Weis, "Thyroid associated orbitopathy," Indian J Ophthalmol, 2012, 60(2): 87-93.

Makinen et al., "Isolated lymphatic endothelial cells transduce growth, survival and migratory signals via the VEGF-C/D receptor VEGFR-3," EMBO J, 2001, 20:4762-4773.

Maruyama et al., "Inflammation-induced lymphangiogenesis in the cornea arises from CD11b-positive macrophages," J Clin Invest, 2005, 115:2363-2372.

Maruyama et al., "The maintenance of lymphatic vessels in the cornea is dependent on the presence of macrophages," Invest Ophthalmol Vis Sci, 2012, 53:3145-3153.

Matos et al., "Protein expression of VEGF, IGF-1 and FGF in retroocular connective tissues and clinical correlation in Graves' ophthalmopathy," Arq. Bras. Oftalmol, 2008, 71: 486-92.

Mourits et al., "Clinical activity score as a guide in the management of patients with Graves' ophthalmopathy," Clin Endocrinol (Oxf), 1997, 47(1):9-14.

Mourits et al., "Clinical criteria for the assessment of disease activity in Graves' ophthalmopathy: a novel approach," Br J Ophthalmol, 1989, 73:639-644.

Nagy et al., "Vascular permeability factor/vascular endothelial growth factor induces lymphangiogenesis as well as angiogenesis," J Exp Med, 2002, 196:1497-1506.

Patel and Dana, "Corneal lymphangiogenesis: implications in immunity," Semin Ophthalmol, 2009, 24:135-138.

Rho et al., "Inhibition of Lymphangiogenesis and Hemangiogenesis in Corneal Inflammation by Subconjunctival Prox1 siRNA Injection in Rats," Invest Ophthalmol Vis Sci, 2015, 56:5871-5879.

Rundle and Wilson, "Development and course of exophthalmos and ophthalmoplegia in Graves' disease with special reference to the effect of thyroidectomy," Clin Sci, 1945, 5(3-4):177-94.

Sakurai et al., "Semaphorin signaling in angiogenesis, lymphangiogenesis and cancer," Cell Research, 2012, 22:23-32.

Sawano, et al., "Flt-1, vascular endothelial growth factor receptor 1, is a novel cell surface marker for the lineage of monocyte-macrophages in humans," Blood, 2001, 97:785-791.

Schacht et al., "Up-regulation of the lymphatic marker podoplanin, a mucin-type transmembrane glycoprotein, in human squamous cell carcinomas and germ cell tumors," Am J Pathol, 2005, 166:913-921.

Seo et al., "MicroRNA miR-466 inhibits lymphangiogenesis by targeting prospero-related homeobox 1 in the alkali burn corneal injury model," J Biomed Sci, 2015, 22:3.

Skobe et al., "Concurrent induction of lymphangiogenesis, angiogenesis, and macrophage recruitment by vascular endothelial growth factor-C in melanoma," Am J Pathol, 2001, 159:893-903.

Suami et al., "The lymphatic territories of the upper limb: anatomical study and clinical implications," Plast Reconstr Surg, 2007, 119:1813-1822.

Verity and Rose, "Acute thyroid eye disease (TED): Principles of medical and surgical management," Eye (Lond.), 2013, 27:308-319.

Werner et al., "Classification of the Eye Changes of Graves' Disease," J Clin Endocrinol Metab, 1969, 29(7):982-4.

Wiersinga et al., Clinical assessment of patients with Graves' orbitopathy: the European Group on Graves' Orbitopathy recommendations to generalists, specialists and clinical researchers, Eur. J. Endocrinol, 2006, 155:387-389.

Wong et al., "Analysis of Orbital Vasculature in Thyroid Orbitopathy by Immunohistochemistry," Sep. 2015, 1 page.

Wong et al., "Orbital angiogenesis and lymphangiogenesis in thyroid eye disease: an analysis of vascular growth factors with clinical correlation," Ophthalmology, Jul. 2016, 123: 2028-2036.

Yang et al., "Understanding Lymphangiogenesis in Knockout Models, the Cornea, and Ocular Diseases for the Development of Therapeutic Interventions," Surv Ophthalmol, 2016, 61(3):272-96.

Ye et al., "Increased serum VEGF and b-FGF in Graves' ophthalmopathy," Graefes Arch Clin Exp Ophthalmol, 2014, 252: 1639-1644.

Zhang et al., "Prognostic significance of VEGF-C, semaphorin 3F, and neuropilin-2 expression in oral squamous cell carcinomas and their relationship with lymphangiogenesis," J Surg Oncol, 2015, 111(4):382-8.

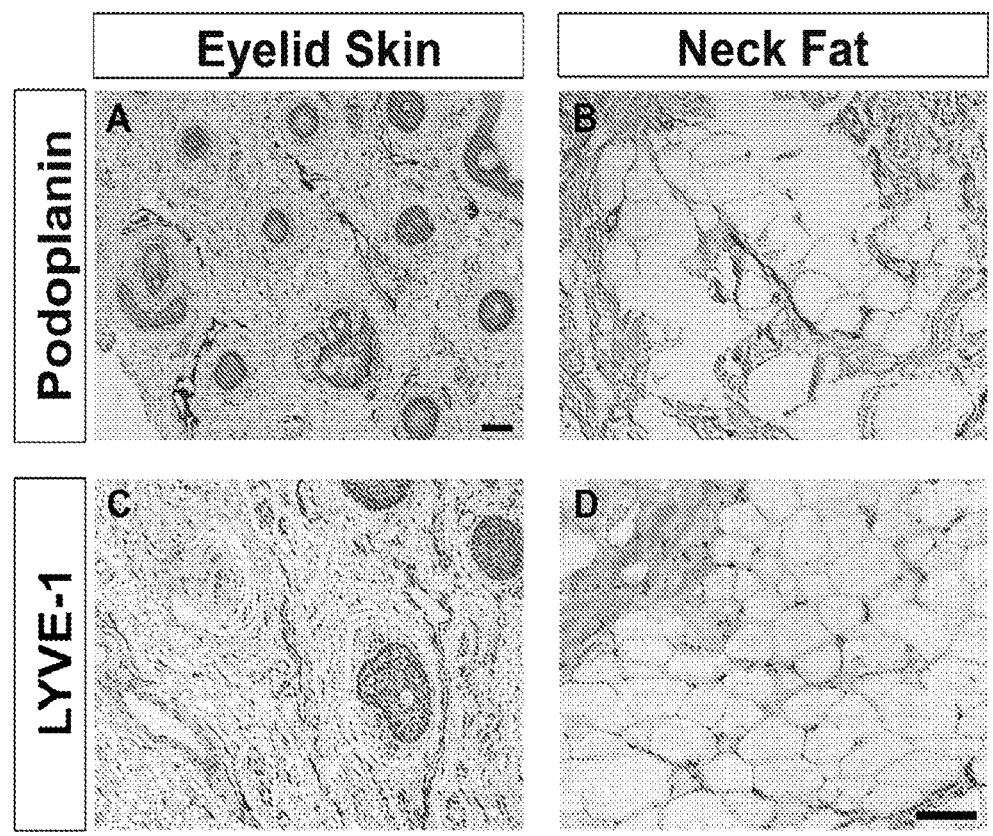
FIGs. 1A-D
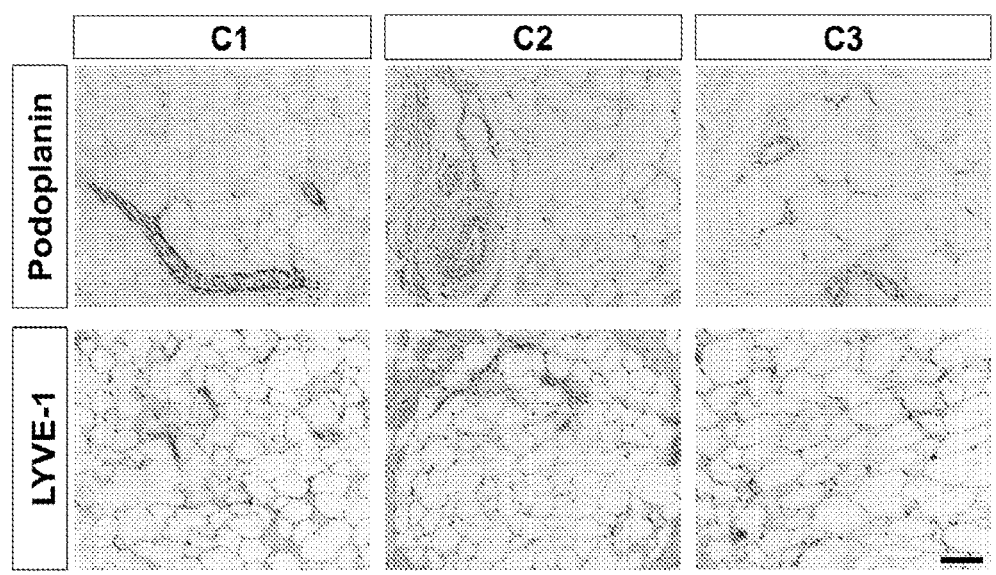
FIG. 2

LOCAL ORBITAL THERAPY FOR THYROID EYE DISEASE

CLAIM OF PRIORITY

This application is a 371 U.S. National Phase Application of PCT/US2017/036517, filed om Jun. 8, 2017, which claims the benefit of U.S. Provisional Patent Application Ser. No. 62/349,273, filed on Jun. 13, 2016. The entire contents of the foregoing are hereby incorporated by reference.

FEDERALLY SPONSORED RESEARCH OR DEVELOPMENT

This invention was made with Government support under Grant Nos. EY005318 and EY027061 awarded by the National Institutes of Health. The Government has certain rights in the invention.

TECHNICAL FIELD

Described herein are methods for treating acute thyroid eye disease (TED) that include administering a composition comprising a VEGF inhibitor and/or a promoter of lymphangiogenesis, and optionally hyaluronidase, by periorbital or intraorbital injection. Also described are compositions comprising a VEGF inhibitor and/or a promoter of lymphangiogenesis and hyaluronidase.

BACKGROUND

Thyroid eye disease (TED), also known as Graves' Ophthalmopathy (GO) and thyroid-associated ophthalmopathy (TAO), is a potentially sight-threatening condition that has perplexed physicians for centuries. The estimated annual incidence rate of TED is 16 cases per 100,000 women and 3 cases per 100,000 men. Approximately 10-20 percent of patients who suffer with this systemic autoimmune condition will develop severe inflammation in the orbit that can lead to disabling double vision or irreversible vision loss.[1] Orbital involvement in TED can consist of extraocular muscle enlargement as well as adipogenesis, the proliferation of fat cells, due to soluble factors upregulated during inflammation and found in the edematous milieu. In severe cases, both of these changes can lead to significant exophthalmos as well as sight threatening optic neuropathy.

SUMMARY

As shown herein, inflamed orbits in acute TED, as compared to chronic TED and control orbits, exhibit increased blood vessels likely mediated by VEGFR-2 and increased VEGF-A signaling. Further, described herein is new evidence of lymphatic vessels in acute TED likely due to elevated expression of pro-lymphangiogenic signaling through VEGF-C and VEGF-D, and possibly through decreased expression of SEMA-3F. These findings suggest anti-angiogenic and/or pro-lymphangiogenic therapy as a means to manage acute TED.

Thus, provided herein are methods for treating acute thyroid eye disease (TED) in a subject. The methods include administering a pharmaceutical composition comprising a therapeutically effective amount of one or both of a VEGF inhibitor and/or a pro-lymphangiogenic agent to the orbit of the eye, e.g., by periorbital or intraorbital injection to a subject in need thereof.

In some embodiments, the VEGF inhibitor specifically inhibits VEGF-A (e.g., does not inhibit VEGF-C or VEGF-D). In some embodiments, the VEGF inhibitor is an anti-VEGF-A antibody. In some embodiments, the anti-VEGF-A antibody is bevacizumab, ranibizumab or aflibercept or an antigen-binding fragment thereof.

In some embodiments, the pro-lymphangiogenic agent is vascular endothelial growth factor C(VEGFC), vascular endothelial growth factor D (VEGFD), soluble Neuropilin 2 (sNRP-2), or anti-semaphorin 3F antibodies and fragments thereof.

In some embodiments, the pharmaceutical composition comprises hyaluronidase, e.g., recombinant human hyaluronidase.

Also provided herein are pharmaceutical composition comprising one, two, or all three of a VEGF inhibitor, a pro-lymphangiogenic agent, and hyaluronidase, e.g., a VEGF inhibitor and a pro-lymphangiogenic agent, a VEGF inhibitor and hyaluronidase, or a pro-lymphangiogenic agent and hyaluronidase.

In some embodiments, the VEGF inhibitor specifically inhibits VEGF-A (e.g., does not inhibit VEGF-C or VEGF-D). In some embodiments, the VEGF inhibitor is an anti-VEGF-A antibody. In some embodiments, the anti-VEGF-A antibody is bevacizumab, ranibizumab or aflibercept or an antigen-binding fragment thereof.

In some embodiments, the pro-lymphangiogenic agent is vascular endothelial growth factor C (VEGFC), vascular endothelial growth factor D (VEGFD), sNRP-2, or anti-semaphorin 3F antibodies and fragments thereof.

In some embodiments, the hyaluronidase is recombinant human hyaluronidase.

Also provided herein is the use of one or both of a VEGF inhibitor and/or a pro-lymphangiogenic agent as described herein for treating acute thyroid eye disease (TED) in a subject, optionally with hyaluronidase.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-D: Immunohistological characterization of control specimens, eyelid skin and subcutaneous fat obtained from the neck. Localization of podoplanin and LYVE-1 confirmed the presence of lymphatic vessels in these samples, as expected, and proved the utility of these markers. Samples were counterstained with hematoxylin. Scale bar=100 μm FIG. 2: Immunohistological characterization of orbital fat obtained from control patients without TED. Staining for podoplanin and LYVE-1 showed no positive staining, indicating the absence of lymphatic vessels, which is consistent with previous reports. Samples were counterstained with hematoxylin. Scale bar=100 μm

DETAILED DESCRIPTION

Figure 3:
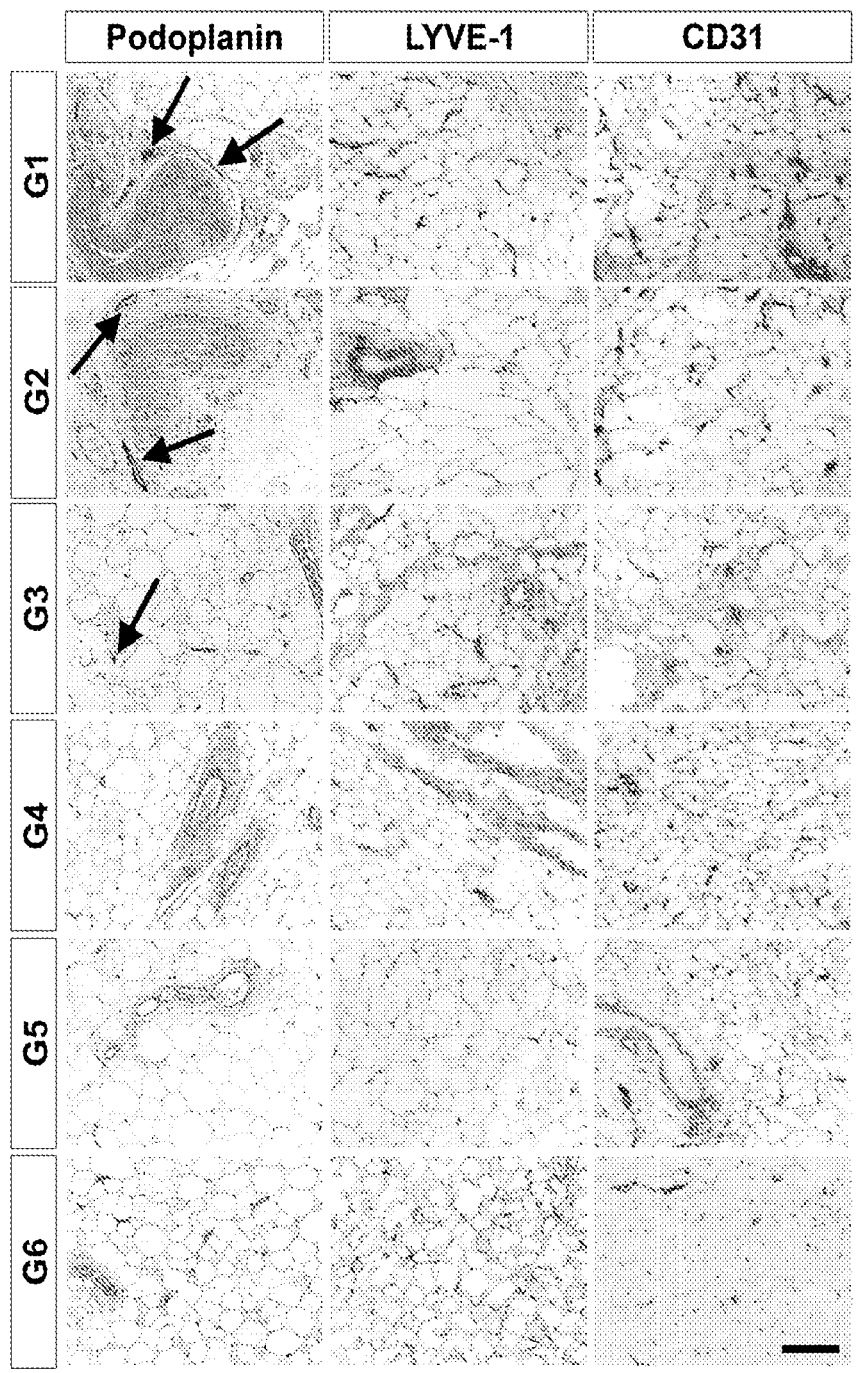
FIG. 3: Immunohistological characterization of orbital fat from patients with TED. Patients G1, G2 and G3 were in the acute, inflammatory phase of the disease and all exhibit podoplanin-positive vessel-like structures (arrows). Patients G4, G5, and G6 are in the chronic stage of disease and do not exhibit any podoplanin-positive cells. Middle and rightmost panels shows LYVE-1 and CD31 staining for patients G1-G6 respectively. Samples are counterstained with hematoxylin. Scale bar=100 µm

The pathogenesis and management of TED have challenged physicians for many years. Although corticosteroids have been used to temporize acute, inflammatory TED, some patients eventually require orbital decompression surgery either urgently for compressive optic neuropathy or in the chronic stage of disease for persistent exophthalmos. Some severe cases of TED are refractory to currently available therapies and a larger proportion of patients with other comorbidities including diabetes are unable to tolerate systemic corticosteroids. See, e.g., Verity and Rose, Eye 27:308-319 (2013).

TED is often characterized by an acute inflammatory phase followed by a prolonged state of chronic inflammation and fibrosis. It is generally during the acute phase when patients may experience the most catastrophic effects of TED. Standard treatment during this acute period consists of systemic corticosteroids, external beam radiation therapy and/or urgent surgical decompression of the orbit. Although these non-targeted therapies can help diminish the inflammatory changes and the ensuing compartment syndrome in the orbit, research has not yet elucidated the factors that make the orbit a unique and susceptible microenvironment for this condition. Previous studies of orbital soft tissues have reported the following: (1) orbital fat and extraocular muscle lack lymphatic vessels,[2] (2) inflammation can induce both angiogenesis and lymphangiogenesis in certain ocular tissues such as the cornea,[3-5] and (3) lymphangiogenesis can occur in orbits that are acutely inflamed from orbital infection.[6]

It is thought that orbital soft tissues do not contain lymphatic vessels except around the dura mater surrounding the optic nerve[7] and the lacrimal gland.[8] In contrast, other fat depots throughout the body contain both blood and lymphatic vessels.[9] The lymphatic system consists of thin-walled, low-pressure vessels that collect and drain protein-rich fluid from the interstitial space and return it to the venous system via the thoracic duct. It plays a dual role as it not only drains interstitial fluid from tissues by way of blind-ended sacs, or terminal lymphatics,[10] but also participates in the immune response. Like angiogenesis, the growth of new blood vessels,[11] lymphangiogenesis, the formation of lymphatic vessels, is modulated by a balance of both stimulators and inhibitors. The endothelial cells (ECs) of blood vessels and lymphatic vessels express common receptors such as vascular endothelial growth factor receptor 2 (VEGFR-2) and neuropilin 2 (NRP-2), and both respond to vascular endothelial growth factor A (VEGF-A).[12] However, lymphatic ECs uniquely express VEGFR-3 that binds VEGF-C and VEGF-D, which is not present on normal blood vessel ECs. The study of lymphatic vessel formation has been facilitated by the identification of a variety of lymphatic EC markers including Prox-1,[13] podoplanin,[14] LYVE-1,[15] and VEGFR-3.[16] Most vascularized tissues, such as subcutaneous and abdominal fat contain lymphatic vessels, yet orbital fat appears to lack lymphatic vessels under normal conditions. Thus, it is plausible to consider that the lack of lymphatic vessels within the orbit may contribute to the pathophysiology of TED.

The best-described mediator of inflammation-induced vascular remodeling is VEGF-A. Its main receptor, VEGFR-2, is expressed on both blood and lymphatic ECs. In addition to stimulating angiogenesis, VEGF-A directly enhances the inflammatory response in tissue. VEGF-A increases vascular permeability,[17] can act as a chemotactic factor for monocytes,[18] and can directly induce expression of adhesion molecules such as the selectins, VE-Cadherin (VE-CAD), VCAM-1, and ICAM-1 in ECs.[19] Besides VEGF-A, other major lymphangiogenic factors include VEGF-C and VEGF-D which bind VEGFR-3 and/or VEGFR-2 receptors expressed by lymphatic ECs and promote their proliferation, migration, and survival.[20, 21] VEGF-C can also act as a chemoattractant of activated macrophages that express VEGFR-3.[22] Understanding these molecular mechanisms may identify targets or agents that regulate blood and lymphatic vessel formation within the orbit in TED, and may alter the clinical course of the disease.

Figure 4:
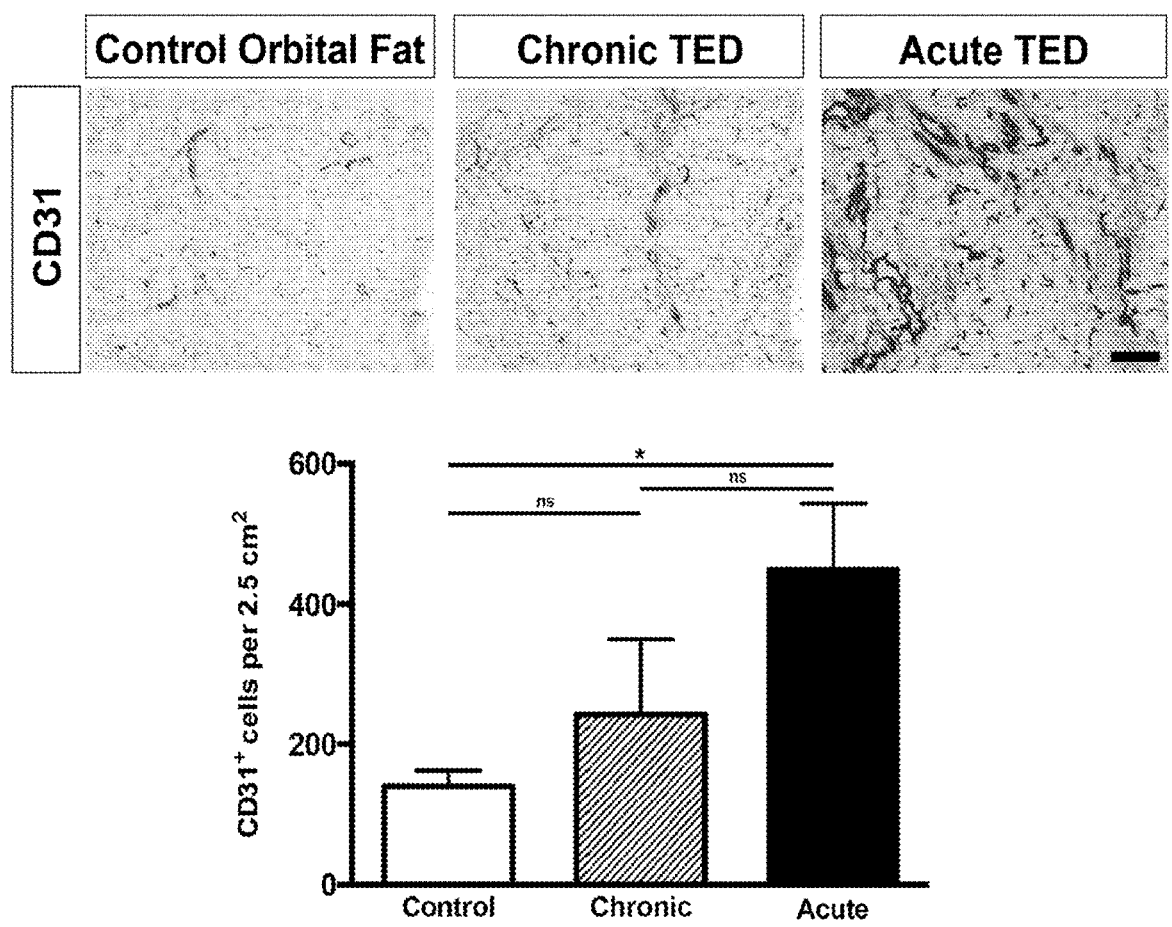
FIG. 4: Increased vasculature in tissue from patients with acute TED. Patients with TED have increased staining of CD31+ cells with dilated blood vessels, when compared against control fat specimens and orbital fat from patients with chronic TED. Quantification of staining revealed a statistically significant increase in CD31+ staining in the acute TED patients when compared against the controls. Samples are counterstained with hematoxylin (blue). Scale bar=100 µm

In order to evaluate whether the etiology of TED might be attributed to the proliferation of blood vessels and/or the absence of native lymphatic capillaries, human orbital tissue specimens obtained from normal controls and subjects with acute and chronic TED were examined using immunohistochemistry, specifically in search of lymphatic vessels. The data demonstrate for the first time that during the acute, inflammatory stage of TED, there is formation of both rare lymphatic vessels and robust blood vessels. There were increased numbers of CD31+ vessels in patients with acute TED and high CAS (FIGS. 3 and 4). Similarly, using the lymphatic markers podoplanin and LYVE-1, the presence of lymphatic vessels was confirmed in control specimens including eyelid skin and subcutaneous fat obtained from the neck (FIG. 1). In contrast, orbital fat obtained from control patients without TED did not exhibit positive podoplanin nor LYVE-1 staining, consistent with previous reports (FIG. 2).[8] In patients with acute TED, lymphatic vessels that were podoplanin positive were detected, while no lymphatic vessels were identified with podoplanin staining in patients with chronic TED (FIG. 3). LYVE-1, on the other hand, which stains both lymphatic capillaries as well as macrophages,[4] exhibited variable, non-specific staining throughout all TED specimens, though the staining appeared to be more robust in single cells in acute TED as opposed to frank vessels. Variable LYVE-1-positive staining in all TED specimens is likely indicative of inflammation-induced macrophage infiltration rather than presence of lymphatic EC.

The VEGF family plays a crucial role in the proliferation of both blood and lymphatic vessels. There are 3 main receptors for VEGF: VEGFR-1, VEGFR-2, and VEGFR-3. VEGFR-1 is a negative regulator of VEGF-A activity in ECs. VEGFR-2 is the predominant effector of VEGF-A's promotion of endothelial cell proliferation and differentiation as well as the primary mediator of VEGF's promotion of vascular permeability. VEGFR-3 regulates lymphendothelial function. The ECs of blood vessels and lymphatic vessels both express some common receptors such as VEGFR-2 and NRP-2, and both respond to VEGF-A.[3] There was elevated mRNA expression of VEGFR-2, but no increased expression of NRP-2 or podoplanin in subjects with acute TED. This is consistent with the histopathological finding that there was increased blood vessel formation and very rare lymphatic vessel formation in patients with acute TED when compared with patients with chronic TED.

VEGF-A is the best-described mediator of inflammation-induced vascular remodeling among all of the VEGF molecules. In addition to stimulating angiogenesis, VEGF-A directly enhances the inflammatory response in tissue by increasing vascular permeability, acting as a chemotactic factor for monocytes,[18] and by directly inducing expression of adhesion molecules such as selectins, VE-CAD, VCAM-1, and ICAM-1 in ECs.[19] The elevated mRNA expression of VEGF-A in patients in the acute inflammatory phase of TED may indicate that these new blood vessels are dilated, leaky, and may cause orbital edema with infiltration of leukocytes, and thereby contributing to the orbital congestion found in TED.

Both VEGF-C[24] and VEGF-D[25] bind VEGFR-2 and VEGFR-3, which are expressed on lymphatic ECs. Experimental models of VEGF-C overexpression in tumor cells have demonstrated increased lymphatic metastasis.[26] Therefore, increased expression of VEGF-C and VEGF-D as found in patients with acute TED suggests the presence of a pro-lymphangiogenic environment. However, histopathologically, we found limited lymphatic vessels in patients with acute TED, and no lymphatic vessels in patients with chronic TED. Limited lymphatic vessel formation may be due to limited expression of VEGFR-3 and NRP-2 confirming the paucity of lymphatic ECs within the orbit. Moreover, SEMA-3F, which is an inhibitor of lymphangiogenesis by competing with VEGF-A, -C, or -D binding to NRP-2[27], trended towards an increased expression in chronic TED. Without wishing to be bound by theory, the potential decrease in SEMA-3F expression in acute TED may account for the formation of some lymphatic vessels in patients with acute TED and be involved in their regression in chronic TED.

Although these studies have shown positive podoplanin staining of orbital adipose tissue in inflamed TED states, these new lymphatic vessels are very rare and they do not appear to impart any functional advantage within the course of the disease as there does not appear to be a functional decompression of these orbits. They exhibited relatively high CAS and needed urgent decompression. This may be due to the fact that there are simply not enough lymphatic vessels to decompress the edematous orbit, or that these are non-functional lymphatic trunks that lack the capillary network to drain interstitial fluid. Regardless, by the time the disease stabilizes and becomes chronic, these lymphatic channels likely regress, as we did not discover any lymphatic vessels in patients with chronic TED.

Similarly, in other ocular tissues that are usually devoid of vascular structures such as the cornea, there has been strong evidence of angiogenesis and lymphangiogenesis within acute, inflammatory conditions using a suture models[5, 28] or alkali burn model.[29, 30] It has been shown that with a temporary insult to the cornea, the outgrowth of blood vessels and lymphatic vessels occur as early as 2 days and peak around day 14. Thereafter, regression of lymphatics starts earlier and is more pronounced than that of blood vessels.[31] Both local anti-angiogenic and anti-lymphangiogenic approaches have been taken in order to regulate potential graft rejection. Similarly, modulation of these angiogenic and lymphangiogenic processes within the orbit is a new therapeutic approaches for TED by decreasing orbital inflammation and edema in acute TED.

Acute TED

As used herein, acute TED is the initial, inflammatory phase of TED characterized by ocular pain, redness, swelling, and impaired function (Rundle and Wilson, Clin Sci. 5(3-4):177-94 (1945); Bothun et al., Clin Ophthalmol. 3: 543-551 (2009); Maheshwari and Weis, Indian J Ophthalmol. 60(2): 87-93 (2012)). Most cases of TED are associated with hyperthyroidism, while the rest are either euthyroid or hypothyroid (Bothun et al., Clin Ophthalmol. 3: 543-551 (2009)). The presence of acute TED can be identified by standard methodology, including the Clinical Assessment Score (Mounts et al., Br. J. Ophthalmol. 73,639-644 (1989); Mounts et al., Clin Endocrinol (Oxf). 47(1):9-14 (1997)), wherein a score of 4 or higher indicates the presence of severe/acute TED.

TABLE 1

Clinical Assessment Score (CAS)

| Category | Description | Points |
|---|---|---|
| Pain | painful, oppressive feeling on or behind the globe, | 1 |
|  | pain on attempted up, side, or down gaze | 1 |
| Redness | redness of the eyelid(s), | 1 |
|  | diffuse redness of the conjunctiva | 1 |
| Swelling | chemosis | 1 |
|  | swollen caruncle | 1 |
|  | edema of the eyelid(s) | 1 |
|  | increase of proptosis of 2 mm or more during a period between 1 and 3 months | 1 |
| Impaired function | decrease in visual acuity of 1 or more lines on the Snellen chart (using a pinhole) during a period between 1 and 3 months | 1 |
|  | decrease of eye movements in any direction equal to or more than 5 degrees during a period of time between 1 and 3 months | 1 |
|  | Total Possible | 10 |

Alternatively, the European Group on Graves' Orbitopathy (EUGOGO) recommendations for assessment of TED can be used, e.g., based on the classical features of inflammation clinical activity score portion (Wiersinge et al., Eur. J. Endocrinol. 155:387-389 (2006)). The maximum score (7) is the sum of all items present, i.e., Spontaneous retrobulbar pain; Pain on attempted up- or down gaze; Redness of the eyelids; Redness of the conjunctiva; Swelling of the eyelids; Inflammation of the caruncle and/or plica; or Conjunctival edema. The presence of a score of 2 or higher indicates the presence of acute TED. The full EUGOGO score can be used to determine the severity of TED in the patient.

The Vision, Inflammation, Strabismus, and Appearance (VISA) score (Dolman and Rootman, Ophthal Plast Reconstr Surg. 22(5):319-24 (2006); Maheshwari and Weis, Indian J Ophthalmol. 60(2):87-93 (2012)) can also be used.

The NOSPECS classification (Werner et al., J Clin Endocrinol Metab. 1969 July; 29(7):982-4) can also be used to determine the severity of TED, i.e., (0): no physical signs or symptoms; (1) only signs, no symptoms (signs limited to upper lid retraction, stare, and lid lag); (2) soft-tissue involvement (symptoms and signs); (3) proptosis; (4) extraocular muscle movement: (5) corneal involvement; (6) sight loss (optic nerve insolvement).

Methods of Treatment

The methods described herein include methods for the treatment of acute TED. Generally, the methods include administering a therapeutically effective amount of a VEGF inhibitor, e.g., a VEGF-A antagonist, e.g., an anti-VEGF-A antibody, as described herein, to a subject who is in need of, or who has been determined to be in need of, such treatment. Alternatively or in addition, the methods can include administering a therapeutically effective amount of a pro-lymphangiogenic agent. In preferred embodiments, the methods include co-administration of hyaluronidase, e.g., concurrently with, or prior or subsequent to (e.g., within 2 hours, one hour, 30 minutes, 15 minutes, 10 minutes, or 5 minutes of) administration of the VEGF inhibitor and/or pro-lymphangiogenic agent.

Subjects that can be treated by the present methods include mammals, e.g., humans and non-human primates, as well as other mammals including veterinary (e.g., pets and livestock) and zoo animals. In preferred embodiments, where a biological agent is administered such as a protein or a nucleic acid, the species of origin of the agent is the same as or closely related to the species of the subject to be treated (i.e., human proteins and nucleic acids are used in humans).

As used in this context, to "treat" means to ameliorate at least one symptom of the disorder associated with TED. Often, acute TED results in ocular pain, redness, swelling, and impaired function; thus, a treatment can result in a reduction in ocular pain, redness, swelling, and impaired function, e.g., an improvement in the CAS, EUGOGO, or NOSPECS score. Administration of a therapeutically effective amount of a VEGF inhibitor and/or a pro-lymphangiogenic agent as described herein for the treatment of TED will result in a reduction in ocular pain, redness, swelling, and impaired function, e.g., an improvement in the CAS, EUGOGO, or NOSPECS score.

In some embodiments, the treatment also includes administration of a standard treatment for TED, e.g., administration of systemic corticosteroids (e.g., hydrocortisone, hydrocortisone acetate, cortisone acetate, tixocortol pivalate, prednisolone, methylprednisolone, and prednisone (see, e.g., Macchia et al., J Endocrinol Invest. 24:152-8 (2001))), external beam radiation therapy and/or urgent surgical decompression (see, e.g., Bothun et al., Clin Ophthalmol. 2009; 3: 543-551; Verity and Rose, Eye 27:308-319 (2013)). Surgical treatments can include orbital decompression surgery, and eye muscle surgery or eyelid surgery (e.g., marginal myotomy of levator palpebrae muscle, lateral tarsal canthoplasty, mullerectomy (resection of the Müller muscle), eyelid spacer grafts, and recession of the lower eyelid retractors). Conservative measures can include elevating the head at night, cool compresses, sunglasses, lubricating eyedrops, and prisms for glasses when the subject has strabismus. Other treatments that can be administered include diuretics to reduce edema; or thyroid ablation, radioactive iodine, methimazole or propylthiouracil (to manage hyperthyroidism).

VEGF Antagonists

Vascular endothelial growth factor (VEGF) was identified and isolated as an endothelial cell-specific mitogen that has the capacity to induce physiological and pathological angiogenesis. In a separate context, a factor that promotes vascular hyperpermeability, initially referred to as "vascular permeability factor," was isolated and later shown to be identical to VEGF. This VEGF is now known as VEGFA and is a member of a larger family of growth factors that also includes VEGFB, VEGFC, VEGFD and placental growth factor (PLGF). These family members differ in their expression pattern, receptor specificity and biological functions. VEGFA, which is often referred to as VEGF, has been studied more than the other members of this family and it has several distinct variants (VEGF121, VEGF145, VEGF148, VEGF165, VEGF183, VEGF189 and VEGF206). These variants occur because of alternative splicing, and they also differ in receptor specificity and function. For a review, see Goel, Hira Lal, and Arthur M. Mercurio. "VEGF targets the tumour cell." Nature Reviews Cancer 13.12 (2013): 871-882. In preferred embodiments, the antagonist specifically inhibits VEGFA, and/or does not inhibit VEGFC/D.

There are two VEGF receptor (VEGFR) tyrosine kinases (RTKs), Flt-1, known also as VEGFR-1 and KDR, Flk-1, or VEGFR-2. VEGFR-2 is the major mediator of the mitogenic, angiogenic, and permeability-enhancing effects of VEGF. For a detailed review of the biological and signaling properties of the VEGFR, see Ferrara and Napoleone, Endocrine reviews 25.4 (2004): 581-611.

As noted above, the methods described herein include administering an effective amount of a VEGF inhibitor to a subject.

In some embodiments, anti-VEGF antibody bevacizumab (AVASTIN), ranibizumab (LUCENTIS) or aflibercept (EYLEA), can be used in the present methods. The antibody bevacizumab and its VEGF-binding activity are reviewed in detail in Ferrara and Napoleone, Endocrine reviews 25.4: 581-611 (2004). Bevacizumab can be administered to a subject, e.g., from 2.5 mg/kg IV to 50 mg/kg IV, for example 5 mg/kg IV, 7.5 mg/kg IV, 10 mg/kg IV, 15 mg/kg IV.

It is to be appreciated, however, that the treatment method described herein can also be performed using other anti-VEGF agents (e.g., VEGF or VEGFR inhibitors, such as, but not limited to, other anti-VEGF antibodies, drugs, prodrugs, small molecules, peptides, nucleic acid inhibitors (e.g., siRNA, shRNA, antisense oligonucleotides), fusion proteins, etc.), e.g., as known in the art, that has the ability to inhibit the action of VEGF (e.g., human VEGF) and/or a VEGFR (e.g., VEGFR-1 and/or VEGFR-2) (e.g., human VEGFR-1 or human VEGFR-2) (i.e., to inhibit VEGF signaling). Assays for determining whether an antibody or other agent interferes with VEGF signaling (either by inhibiting VEGF or a VEGFR or the interaction between VEGF and its receptor), for example, are well known in the art, and can be used to determine whether an anti-VEGF agent interferes with VEGF signaling and is therefore encompassed by the presently disclosed methods. Non-limiting examples of such assays include the VEGF inhibition assays described in Foy, Kevin C., et al. "Combined vaccination with HER-2 peptide followed by therapy with VEGF peptide mimics exerts effective anti-tumor and anti-angiogenic effects in vitro and in vivo." Oncoimmunology 1.7 (2012): 1048-1060 and Brekken, Rolf A., et al. "Selective inhibition of vascular endothelial growth factor (VEGF) receptor 2 (KDR/Flk-1) activity by a monoclonal anti-VEGF antibody blocks tumor growth in mice." Cancer research 60.18 (2000): 5117-5124.

By way of non-limiting example, other anti-VEGF antibodies and inhibitors that are known in the art, and, that can be used in the methods disclosed herein include but are not limited to: bevacizumab, ranibizumab, pegaptanib, imatinib, vandetanib, sorafenib, pazopanib, valatanib, vevasiranib, aflibercept, etanercept, anecortave acetate (angiostatic steroid), VEGF-trap (a fusion protein), squalamine lactate, erlotinib, gefitinib (small molecules), Combretastatin A4 Prodrug (an antitubulin/antiangiogenic agent), AdPEDF (Adenovector pigment epithelium-derived factor), Cand5 (siRNA), protein tyrosine kinase 7 inhibitors (PTK7), lipolytic agents, TG100801, AG013958, AL39324, AGN211745 (VEGF receptor blockers), anti-angiogenic VEGF-A(xxx)b family, VEGF Trap (receptor decoy, aflibercept), protein kinase antibodies to tyrosine kinase inhibitor receptors SIM010603, kinase domain receptor antibodies (KDR1.3 and KDR2.6), GS101 aganirsen (an antisense oligonucleotide against insulin receptor substrate aka IRS-1), picropodophyllin (PPP), tetrameric tripeptide, tissue kallikrein, KH906 (a recombinant human VEGF receptor protein fusion), beta-adreno receptor blocker β3-AR, nicotinic acetycholine receptor antagonists, linomide analogue (Lin05), morpholino oligomers (VEGFR1_MOe13), decursin, prorenin, vasohibin and sirolimus. It will be appreciated that because the amino acids sequences (as well as nucleic acid sequences encoding the amino acid sequences) of VEGF and VEGFRs are known in the art, the skilled artisan can readily design additional anti-VEGF agents for use in the presently disclosed methods.

Dosage ranges for anti-VEGF agents, e.g., those disclosed above, can be readily determined by the ordinarily skilled artisan, and can, e.g., first be determined in animal models for determining dosage, safety and efficacy according to standard methods known in the art.

Pro-Lymphangiogenic Agents

Stimulating lymphangiogenesis, the growth of lymphatic vessels, can also be used to relieve the symptoms of TED. Thus the present methods can also include the administration of pro-lymphangiogenic agents such as VEGF-C, VEGF-D, and/or anti-Semaforin 3F antibodies. See, e.g., Karkkainen et al. (2001) Trends in Molecular Medicine 7(1):18-22; Zhang et al., J Surg Oncol. (2015) 111(4):382-8; Sakurai et al. (2012). Cell Research 22:23-32; and Yang et al. (2016) Sury Ophthalmol. 61(3):272-96.

VEGFC/VEGFD

The sequence of the VEGFC preprotein is as follows:

```
                                                          (SEQ ID NO: 1)
  1 mhllgffsva csllaaallp gpreapaaaa afesgldlsd aepdageata yaskdleeql 61 rsvssvdelm tvlypeywkm ykcqlrkggw qhnreqanln srteetikfa aahynteilk 121 sidnewrktq cmprevcidv gkefgvatnt ffkppcvsvy rcggccnseg lqcmntstsy 181 lsktlfeitv plsqgpkpvt isfanhtscr cmskldvyrq vhsiirrslp atlpqcqaan 241 ktcptnymwn nhicrclaqe dfmfssdagd dstdgfhdic gpnkeldeet cqcvcraglr 301 pascgphkel drnscqcvck nklfpsqcga nrefdentcq cvckrtcprn qplnpgkcac 361 ectespqkcl lkgkkfhhqt cscyrrpctn rqkacepgfs yseevcrcvp sywkrpqms
```

The mature VEGFC is amino acids 112 to 227 of SEQ ID NO:1. Amino acids 1-31 are a signal peptide and can be deleted. Thus, in the present methods VEGFC can be, e.g., a peptide of SEQ ID NO:1, of amino acids 32-419 of SEQ ID NO:1, or amino acids 112-227 of SEQ ID NO:1. The VEGFC can be natural, recombinant or synthetic, and can be produced and isolated and purified using methods known in the art.

The sequence of the VEGFD preprotein is as follows:

```
                                                          (SEQ ID NO: 2)
  1 myrewvvvnv fmmlyvqlvq gssnehgpvk rssqstlers eqqiraassl eellrithse 61 dwklwrcrlr lksftsmdsr sashrstrfa atfydietlk videewqrtq cspretcvev 121 aselgkstnt ffkppcvnvf rcggccnees licmntstsy iskqlfeisv pltsvpelvp 181 vkvanhtgck clptaprhpy siirrsiqip eedrcshskk lcpidmlwds nkckcvlqee 241 nplagtedhs hlqepalcgp hmmfdedrce cvcktpcpkd liqhpkncsc feckesletc 301 cqkhklfhpd tcscedrcpf htrpcasgkt acakhcrfpk ekraaqgphs rknp
```

The mature VEGFD is amino acids 89 to 205 of SEQ ID NO:2. Amino acids 1-21 are a signal peptide and can be deleted. Thus, in the present methods VEGFC can be, e.g., a peptide of SEQ ID NO:1, of amino acids 22-354 of SEQ ID NO:2, or amino acids 89-205 of SEQ ID NO:2. The VEGFD can be natural, recombinant or synthetic, and can be produced and isolated and purified using methods known in the art.

The present methods can include administration of a VEGFC or VEGFD peptide, or a nucleic acid encoding a VEGFC or VEGFD peptide, e.g., a peptide as described herein. GenBank Ref. No. NM_005429.4 provides an exemplary mRNA sequence encoding VEGFC preprotein. GenBank Ref. No. NM_004469.4 provides an exemplary mRNA sequence encoding VEGFD preprotein. The nucleic acid encoding the VEGFC and/or VEGFD can be, e.g., in an expression vector. Thus, the methods can include delivery of an expression vector for in vivo transfection and expression of a polynucleotide that encodes a VEGFC/VEGFD peptide or active fragment thereof, as described herein. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988);

Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., a VEGFC or VEGFD nucleic acid) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21):1867-74 (2000).

In some embodiments, a gene encoding VEGFC or VEGFD is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Semaphorin 3F

Semaphorin 3F has three variants; the sequences are in GenBank at the following Accession numbers:

| Variant/Isoform | mRNA Acc. No. | Protein Acc. No. |
|---|---|---|
| 1 | NM_004186.4 | NP_004177.3 |
| 2 | NM_001318800.1 | NP_001305729.1 |
| 3 | NM_001318798.1 | NP_001305727.1 |

Methods for making anti-semaphorin 3F antibodies and fragments thereof that bind specifically to SEMA 3F and inhibit its anti-lymphangiogenic activity are well known in the art, and suitable antibodies are commercially available as well, e.g., from Novus Biologicals, R&D systems, LifeSpan Biosciences, Abnova, Abcam, Santa Cruz Biotechnology, Inc. and EMD Millipore.

The methods can also include administration of soluble Neuropilin 2 (sNRP-2) as a potential anti-SEMA3F agent. Neuropilin2 is the receptor for SEMA3F, so soluble Neuropilin 2 can act as a trap, providing another way to regulate SEMA3F. See, e.g., Rossignol et al., Genomics. 2000; 70:211-222; Fassold et al., Arthritis Rheum. 2009 October; 60(10):2892-901.

The methods can include administration of a sNRP-2 peptide, or a nucleic acid encoding the sNRP-2 peptide, as described above for VEGFC and VEGFD.

Exemplary sequence for sNRP-2 includes GenBank Acc. No. AAG41405.1:

```
                                                      (SEQ ID NO: 1)
  1 mdmfpltwvf lalyfsrhqv rgqpdppcgg rlnskdagyi tspgypqdyp shqncewivy 61 apepnqkivl nfnphfeiek hdckydfiei rdgdsesadl lgkhcgniap ptiissgsml 121 yikftsdyar qgagfslrye ifktgsedcs knftspngti espgfpekyp hnldctftil 181 akpkmeiilq flifdlehdp lqvgegdcky dwldiwdgip hvgpligkyc gtktpselrs 241 stgilsltfh tdmavakdgf saryylvhqe plenfqcnvp lgmesgrian eqisasstys 301 dgrwtpqqsr lhgddngwtp nldsnkeylq vdlrfltmlt aiatqgaisr etqngyyvks 361 yklevstnge dwmvyrhgkn hkvfqannda tevvlnklha plltrfvrir pqtwhsgial 421 rlelfgcrvt dapcsnmlgm lsgliadsqi sasstqeylw spsaarlvss rsgwfpripq 481 aqpgeewlqv dlgtpktvkg viiqgarggd sitavearaf vrkfkvsysl ngkdweyiqd 541 prtqqpkvgc swrpl
```

In some embodiments, the first 1-28 amino acids are deleted. The sNRP-2 peptides can be natural, recombinant or synthetic, and can be produced and isolated and purified using methods known in the art.

Pharmaceutical Compositions and Methods of Administration

The methods described herein include the use of pharmaceutical compositions comprising a VEGF antagonist and/or a pro-lymphangiogenic agent as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., corticosteroids.

In preferred embodiments, the compositions include hyaluronidase. Animal-derived hyaluronidases include HYDASE (Akorn Inc.); VITRASE (Bausch+Lomb/Valeant Pharmaceuticals); AMPHADASE (Amphastar Pharmaceuticals); and WYDASE. Synthetic (recombinant or rDNA) "human" hyaluronidases include HYLENEX (Halozyme Therapeutics).

Pharmaceutical compositions are typically formulated to be compatible with its intended route of administration, i.e., periorbital or intraorbital injection in the present case.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, solutions or suspensions used for periorbital or intraorbital injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including gels, matrices, implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Methods

The following materials and methods were used in the examples set forth below.

Human Subjects and Specimen Collection

Orbital fat samples were obtained from patients undergoing either urgent or elective orbital decompression for TED by three surgeons at Massachusetts Eye and Ear (MEE) between 2012 and 2016. Patients were excluded if they had previous radiation to the orbit, previous unrelated orbital surgery or trauma (not including strabismus surgery), or previous orbital infection. We included patients regardless of whether they were or were not on steroids at the time of decompression surgery. Smoking status was noted, but was not considered in the inclusion or exclusion criteria.

Control samples included eyelid skin, eyelid pre-aponeurotic fat, and subcutaneous neck fat from patients without thyroid disease undergoing unrelated procedures (blepharoplasty and excision of prolapsed orbital fat) as well as cadaveric orbital fat from patients without thyroid disease. Electronic medical records were reviewed for demographic information, prior history of medical and surgical treatments for thyroid disease, clinical exam findings and photos. Clinical Activity Score (CAS) was calculated for each patient based on documented exam findings and photographs according to Mounts and colleagues (Table 1).[23] Collection and evaluation of protected patient health information were in compliance with the rules and regulations of the Health Insurance Portability and Accountability Act. The MEE and the Massachusetts General Hospital Human Studies Committee completed an administrative review of the study and Institutional Review Board (IRB) approval was obtained. Informed consent was obtained from each subject for use of tissue for research purposes. All procedures performed in studies involving human participants were in accordance with the ethical standards of the institutional research committee and with the 1964 Helsinki declaration and its later amendments or comparable ethical standards.

Immunohistochemistry (IHC)

Tissue specimens were collected and processed as either formalin-fixed paraffin-embedded sections (FFPE) or cryosections. For FFPE sections, serial sections (4 μm) were cut and deparaffinized in 100% xylene, then rehydrated in a series of ethanol and washed with PBS. Slides were incubated in 3% $H_2O_2$ in methanol to block endogenous peroxidases and blocked in TNB protein blocking solution (Thermo-Fisher Scientific, Waltham, Mass.). Primary antibody (podoplanin 1:25, Covance Laboratories, Dedham, Mass.) was incubated overnight at 4° C. The following day, sections were incubated in biotinylated secondary antibody (1:200, Vector Laboratories, Burlingame, Calif.) followed by alkaline phosphatase-conjugated avidin (Vectastain ABC-AP Universal Kit; Vector Laboratories, Burlingame, Calif.). Expression was visualized with the Vector Red chromogenic substrate kit (Vector Laboratories, Burlingame, Calif.) and counterstaining was performed using Gill no. 3 hematoxylin (Sigma-Aldrich, St. Louis, Mo.).

For frozen tissue, serial cryosections (8-10 μm) were cut and stored at −80° C. prior to use. Slides were air-dried at room temperature (RT), fixed in 100% acetone, washed with PBS, incubated in 3% $H_2O_2$ in methanol, and blocked in TNB. Primary antibodies CD31 (1:200 Dako, Carpinteria, Calif.) and LYVE-1 (1:200 ReliaTech GmbH, Wolfenbuttel, Germany) were added for two hours at RT. Sections were then incubated in biotinylated secondary antibody (1:200, Vector Laboratories, Burlingame, Calif.) followed by alkaline phosphatase-conjugated avidin. Vector Red chromogenic substrate kit was used for visualization followed by a counterstain with Gill no. 3 hematoxylin. All imaging was performed using an Axioskop 2 MOT Plus microscope (Carl Zeiss Inc., Thornwood, N.Y.).

RNA Extraction and Quantitative Real-Time PCR (qPCR)

Total RNA was extracted from samples using TRIzol® (Invitrogen, Carlsbad, Calif.) and PureLink® RNA Mini Kit (Ambion, Foster City, Calif.). Primers for VEGFR-1, VEGFR-2, VEGFR-3, NRP1, NRP2, SEMA3F, VEGF-A, VEGF-C, VEGF-D, podoplanin, and LYVE-1 were designed using the MGH Primer Bank. cDNA was prepared using 800 ng of RNA using the iScript cDNA synthesis kit (Bio-Rad Laboratories, Inc., Hercules, Calif.) and probed for qRT-PCR using Faststart Universal SYBR Green Master (Hoffmann-La Roche, Basel, Switzerland). Fold changes were calculated as the ratio of $2^{-\Delta\Delta Ct}$ and normalized to the housekeeping genes GAPDH, HPRT1 and B2M and compared between acute (CAS>4) and chronic (CAS<4) cases of TED, and normal control specimens.

Example 1. Clinical Demographics

Tissues from 15 TED patients (G1-15) and control orbital tissue samples (C1-4) were included as specimens in this study and their clinical and demographic information is summarized in Table 2. A majority of the patients were female (11/15). Ages ranged from 33 to 77 years with a mean of 55.9±13.5 years. Among the 15 patients, 7 had acute compressive optic neuropathy (CON) requiring an urgent orbital decompression. All of the patients with CON were found to have a CAS of 5 or greater (see Table 1 for details on CAS formulation) with a mean score of 5.8±1.0. One additional patient was in the acute phase of TED but did not have CON. The remaining seven patients who underwent balanced decompression for stable exophthalmos during the chronic phase had CAS ranging from 1 to 3 with an average of 1.9±0.7. All but one patient received systemic treatment for their Graves' disease. With regard to the elapsed time from initial onset of symptoms of TED to surgical management, patients with active disease had an average of 9 months and the chronic group waited an average of 38 months.

Four control specimens were obtained from cadaveric intraconal fat (C2 and C3) or from live patients undergoing removal of prolapsed orbital fat (C1 and C4). There were three male and one female control subjects with ages ranging from 41 to 69 years (mean 56.3 years). None of these subjects had a history of thyroid disease or TED.

TABLE 2

Clinical Characteristics

| Patient | Gender | Age | Laterality | Thyroid treatment | Time dx to surgery | Steroids Y/N | Smoking Y/N | CON | CAS |
|---|---|---|---|---|---|---|---|---|---|
| C1 | F | 69 | N/A | N/A | N/A | N | Unk | N/A | N/A |
| C2 | M | 54 | N/A | N/A | N/A | N | Unk | N/A | N/A |
| C3 | M | 41 | N/A | N/A | N/A | N | Unk | N/A | N/A |
| C4 | M | 61 | N/A | N/A | N/A | N | Unk | N/A | N/A |
| G1 | F | 59 | OU | RAI, methimazole, thyroidectomy | 13 mo | Y | N | Y | 7 |
| G2 | M | 49 | OU | Tapazole | 10 mo | Y | N | Y | 5 |
| G3 | F | 58 | OS | Methimazole | 9 mo | Y | Y | Y | 7 |
| G4 | M | 48 | OD | Methimazole | 10 mo | N | Y | N | 2 |
| G5 | F | 67 | OU | RAI | 36 mo | N | Y | N | 1 |
| G6 | F | 35 | OU | Methimazole, propranolol | 13 mo | N | N | N | 1 |
| G7 | F | 65 | OU | none | 3 mo | Y | N | Y | 5 |
| G8 | F | 70 | OU | Methimazole | 4 mo | Y | N | N | 2 |
| G9 | F | 64 | OS | Methimazole | 3 mo | N | N | Y | 7 |
| G10 | M | 49 | OU | Tapazole | 20 mo | Y | N | Y | 5 |
| G11 | F | 61 | OU | RAI | 2 mo | Y | Y | Y | 5 |
| G12 | F | 66 | OU | Thyroidectomy | 15 mo | N | N | N | 5 |
| G13 | F | 33 | OU | RAI | 84 mo | N | N | N | 2 |

TABLE 2-continued

Clinical Characteristics

| Patient | Gender | Age | Laterality | Thyroid treatment | Time dx to surgery | Steroids Y/N | Smoking Y/N | CON | CAS |
|---|---|---|---|---|---|---|---|---|---|
| G14 | M | 37 | OS | Thyroidectomy | 96 mo | N | N | N | 3 |
| G15 | F | 77 | OU | Methimazole | 24 mo | Y | N | N | 2 |

CAS = clinical activity score;
CON = compressive optic neuropathy;
F = Female;
M = male;
mo = month;
N = no;
N/A = not applicable;
OD = right eye;
OS = left eye;
OU = both eyes;
RAI = radioactive iodine;
Unk = unknown;
Y = yes Example 2. Immunohistological Characterization of Lymphatic Vessels Tissues with known lymphatic vessels were stained with podoplanin and LYVE-1 as positive controls (FIGS. 1A-D). Eyelid skin from blepharoplasty specimens clearly showed positive staining along open-lumened, vessel-like structures with both podoplanin and LYVE-1 (FIG. 1A, 1C). Subcutaneous neck fat also showed positive podoplanin staining in vessels though there were fewer lymphatic structures within this tissue (FIG. 1B). LYVE-1 staining of neck fat revealed small vascular structures as well as staining of single cells suggestive of macrophages and/or lymphatic capillaries (FIG. 1D).

Podoplanin and LYVE-1 were used to stain control periocular fat from patients with prolapsed orbital fat and from cadaver intraconal orbital fat (FIG. 2) as negative controls. In these control specimens, there was no positive staining in areas that contained vascular structures, which is consistent with previous reports.

When evaluating the first six patients with Graves' disease and TED (G1-G6), podoplanin staining only identified rare lymphatic vessels in G1, G2, and G3 which were acute TED patients who underwent urgent decompression for compressive optic neuropathy with a CAS of 7, 5, and 7, respectively (FIG. 3). The lymphatic vessel staining failed to identify any positive vessels in the last three patients with chronic TED who underwent elective decompression for chronic disease (G4-G6), with a CAS of 2, 1, and 1 respectively.

Example 3. Immunohistological Characterization of Quantification of CD31+ Vessels In the inflamed orbit of patients with acute TED, there appeared to be evidence of rare but new lymphatic vessel formation. This prompted investigation of potential blood vessel formation within acute TED. There was significantly increased expression of the pan-endothelial cell marker CD31 in acute TED (G1-G3) compared to chronic TED (G4-G6) (FIG. 3, rightmost column) and normal controls (FIG. 4). Quantification of CD31+ staining of orbital fat samples revealed an average of 140 CD31+ cells per 2.5 cm$^2$ in the control, 242 CD31+ cells per 2.5 cm$^2$ in the chronic TED patients, and 448 CD31+ cells per 2.5 cm$^2$ in the acute TED patients (FIG. 4). There was a statistically significant increase in CD31+ staining in the acute TED patients when compared against the controls. These data suggest that the surge in CD31 expression, especially in the acute, inflammatory phase of TED, signifies angiogenesis and these new vessels are somewhat sustained in the chronic phase compared to controls.

Example 4. qRT-PCR Analysis of Orbital Specimens

Figure 5:
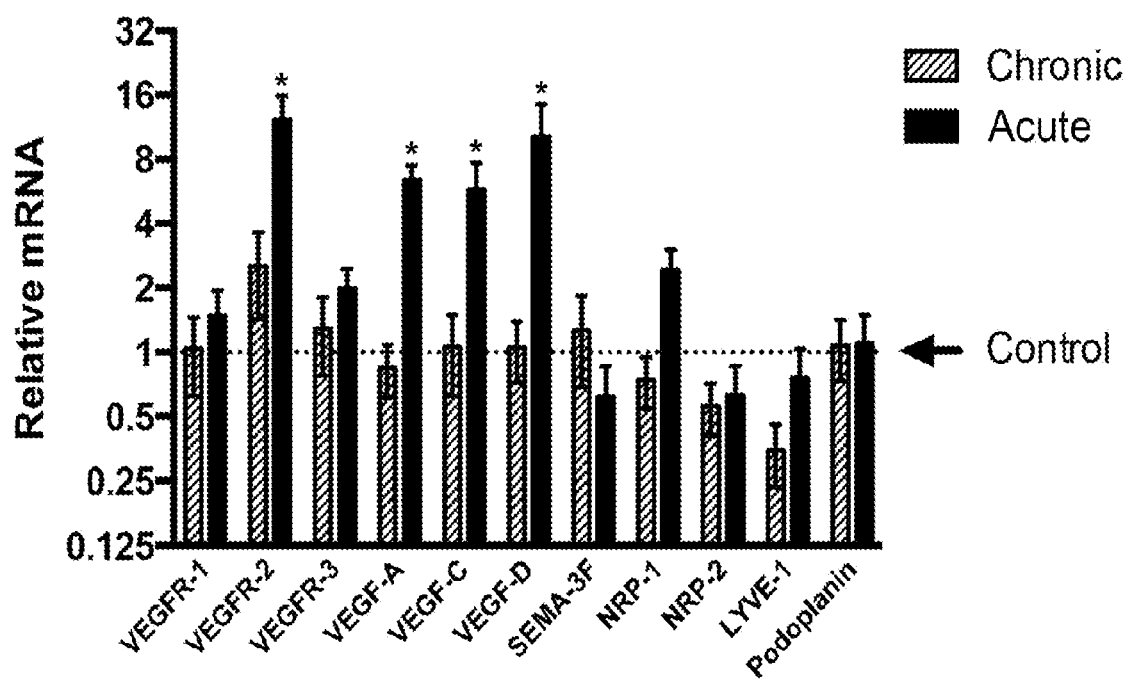
FIG. 5: Changes in gene expression associated with TED. Orbit specimens of five patients with acute TED (CAS>4) and five patients with chronic TED (CAS<4) were collected and relative mRNA expression was evaluated. The values were averaged within the chronic and acute groups. qRT-PCR analysis of genes revealed a significant increase in expression of VEGFR-2, VEGF-A, VEGF-C, and VEGF-D in acute TED when compared to chronic disease and control specimens.

Patients with acute TED (CAS>4): subjects G3, G7, G9, G11, G12, and patients with chronic TED (CAS<4): subjects G6, G8, G13, G14, G15, were grouped and relative mRNA expression of VEGF, VEGF receptors, SEMA-3F, NRP-1, NRP-2, LYVE-1 and podoplanin were evaluated (FIG. 5). There was no statistically significant difference between acute and chronic TED in the expression of VEGFR-1 and VEGFR-3. In contrast, there was a significant 12.24±3.57-fold increase in VEGFR-2 expression within the acute TED patients when compared to control, while there was only a 2.53±1.10-fold increase of VEGFR-2 expression within patients with chronic TED compared to control. In addition, there was a significant relative increase in VEGF-A (6.41±1.10 fold), VEGF-C (5.78±1.92 fold), and VEGF-D (10.17±0.17 fold) mRNA expression in the acute TED patients when compared to control. Within patients with chronic TED, there was no significant increase in VEGF-A (0.84±0.23), VEGF-C (1.10±0.44), and VEGF-D (1.05±0.33) mRNA expression. In addition, there was a trend toward increased expression of NRP-1 and LYVE-1 in the acute TED patients when compared against chronic TED. A significant difference in NRP-2 or podoplanin expression between the two cohorts was not seen. Intriguingly, there appeared to be a trend towards increased mRNA expression of SEMA-3F, an inhibitor of lymphangiogenesis, in chronic TED subjects when compared against acute TED subjects.

REFERENCES

1. Bahn R S. Graves' ophthalmopathy. N Engl J Med. 2010; 362:726-738.
2. Gausas R E. Advances in applied anatomy of the eyelid and orbit. Curr Opin Ophthalmol. 2004; 15:422-425.
3. Patel S P, Dana R. Corneal lymphangiogenesis: implications in immunity. Semin Ophthalmol. 2009; 24:135-138.

4. Maruyama K, Ii M, Cursiefen C, et al. Inflammation-induced lymphangiogenesis in the cornea arises from CD11b-positive macrophages. J Clin Invest. 2005; 115:2363-2372.
5. Maruyama K, Nakazawa T, Cursiefen C, et al. The maintenance of lymphatic vessels in the cornea is dependent on the presence of macrophages. Invest Ophthalmol Vis Sci. 2012; 53:3145-3153.
6. Fogt F, Zimmerman R L, Daly T, Gausas R E. Observation of lymphatic vessels in orbital fat of patients with inflammatory conditions: a form fruste of lymphangiogenesis? Int J Mol Med. 2004; 13:681-683.
7. Killer H E, Laeng H R, Groscurth P. Lymphatic capillaries in the meninges of the human optic nerve. J Neuroophthalmol. 1999; 19:222-228.
8. Gausas R E, Gonnering R S, Lemke B N, Dortzbach R K, Sherman D D. Identification of human orbital lymphatics. Ophthal Plast Reconstr Surg. 1999; 15:252-259.
9. Harvey N L. The link between lymphatic function and adipose biology. Ann N Y Acad Sci. 2008; 1131:82-88.
10. Suami H, Taylor G I, Pan W R. The lymphatic territories of the upper limb: anatomical study and clinical implications. Plast Reconstr Surg. 2007; 119:1813-1822.
11. Folkman J. Fundamental concepts of the angiogenic process. Curr Mol Med. 2003; 3:643-651.
12. Nagy J A, Vasile E, Feng D, et al. Vascular permeability factor/vascular endothelial growth factor induces lymphangiogenesis as well as angiogenesis. J Exp Med. 2002; 196:1497-1506.
13. Hong Y K, Detmar M. Prox1, master regulator of the lymphatic vasculature phenotype. Cell Tissue Res. 2003; 314:85-92.
14. Schacht V, Dadras S S, Johnson L A, Jackson D G, Hong Y K, Detmar M. Up-regulation of the lymphatic marker podoplanin, a mucin-type transmembrane glycoprotein, in human squamous cell carcinomas and germ cell tumors. Am J Pathol. 2005; 166:913-921.
15. Detmar M, Hirakawa S. The formation of lymphatic vessels and its importance in the setting of malignancy. J Exp Med. 2002; 196:713-718.
16. Kaipainen A, Vlaykova T, Hatva E, et al. Enhanced expression of the tie receptor tyrosine kinase mesenger RNA in the vascular endothelium of metastatic melanomas. Cancer Res. 1994; 54:6571-6577.
17. Keck P J, Hauser S D, Krivi G, et al. Vascular permeability factor, an endothelial cell mitogen related to PDGF. Science. 1989; 246:1309-1312.
18. Sawano A, Iwai S, Sakurai Y, et al. Flt-1, vascular endothelial growth factor receptor 1, is a novel cell surface marker for the lineage of monocyte-macrophages in humans. Blood. 2001; 97:785-791.
19. Detmar M, Brown L F, Schon M P, et al. Increased microvascular density and enhanced leukocyte rolling and adhesion in the skin of VEGF transgenic mice. J Invest Dermatol. 1998; 111:1-6.
20. Achen M G, Jeltsch M, Kukk E, et al. Vascular endothelial growth factor D (VEGF-D) is a ligand for the tyrosine kinases VEGF receptor 2 (Flk1) and VEGF receptor 3 (Flt4). Proc Natl Acad Sci USA. 1998; 95:548-553.
21. Makinen T, Veikkola T, Mustjoki S, et al. Isolated lymphatic endothelial cells transduce growth, survival and migratory signals via the VEGF-C/D receptor VEGFR-3. EMBO J. 2001; 20:4762-4773.
22. Skobe M, Hamberg L M, Hawighorst T, et al. Concurrent induction of lymphangiogenesis, angiogenesis, and macrophage recruitment by vascular endothelial growth factor-C in melanoma. Am J Pathol. 2001; 159:893-903.
23. Mourns M P, Koornneef L, Wiersinga W M, Prummel M F, Berghout A, van der Gaag R. Clinical criteria for the assessment of disease activity in Graves' ophthalmopathy: a novel approach. Br J Ophthalmol. 1989; 73:639-644.
24. Karkkainen M J, Haiko P, Sainio K, et al. Vascular endothelial growth factor C is required for sprouting of the first lymphatic vessels from embryonic veins. Nat Immunol. 2004; 5:74-80.
25. Haiko P, Makinen T, Keskitalo S, et al. Deletion of vascular endothelial growth factor C (VEGF-C) and VEGF-D is not equivalent to VEGF receptor 3 deletion in mouse embryos. Mol Cell Biol. 2008; 28:4843-4850.
26. Huggenberger R, Siddiqui S S, Brander D, et al. An important role of lymphatic vessel activation in limiting acute inflammation. Blood. 2011; 117:4667-4678.
27. Bielenberg D R, Hida Y, Shimizu A, et al. Semaphorin 3F, a chemorepulsant for endothelial cells, induces a poorly vascularized, encapsulated, nonmetastatic tumor phenotype. J Clin Invest. 2004; 114:1260-1271.
28. Bock F, Onderka J, Dietrich T, et al. Bevacizumab as a potent inhibitor of inflammatory corneal angiogenesis and lymphangiogenesis. Invest Ophthalmol Vis Sci. 2007; 48:2545-2552.
29. Rho C R, Choi J S, Seo M, Lee S K, Joo C K. Inhibition of Lymphangiogenesis and Hemangiogenesis in Corneal Inflammation by Subconjunctival Prox1 siRNA Injection in Rats. Invest Ophthalmol Vis Sci. 2015; 56:5871-5879.
30. Seo M, Choi J S, Rho C R, Joo C K, Lee S K. MicroRNA miR-466 inhibits Lymphangiogenesis by targeting prospero-related homeobox 1 in the alkali burn corneal injury model. J Biomed Sci. 2015; 22:3.
31. Cursiefen C, Maruyama K, Jackson D G, Streilein J W, Kruse F E. Time course of angiogenesis and lymphangiogenesis after brief corneal inflammation. Cornea. 2006; 25:443-447.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating acute thyroid eye disease (TED) in a subject, the method comprising administering a pharmaceutical composition comprising a therapeutically effective amount of an anti-VEGF-A antibody by periorbital or intraorbital injection to a subject in need thereof.

2. The method of claim 1, wherein the anti-VEGF-A antibody is bevacizumab, ranibizumab, or an antigen-binding fragment thereof.

3. The method of claim 1, wherein the pharmaceutical composition further comprises hyaluronidase.

4. A method of treating acute thyroid eye disease (TED) in a subject, the method comprising administering a pharmaceutical composition comprising a therapeutically effective amount of aflibercept by periorbital or intraorbital injection to a subject in need thereof.

5. The method of claim 4, wherein the pharmaceutical composition further comprises hyaluronidase.

* * * * *

UNITED STATES PATENT AND TRADEMARK OFFICE
CERTIFICATE OF CORRECTION

PATENT NO. : 10,906,969 B2
APPLICATION NO. : 16/307411
DATED : February 2, 2021
INVENTOR(S) : N. Grace Lee et al.

It is certified that error appears in the above-identified patent and that said Letters Patent is hereby corrected as shown below:

In the Specification

In Column 1, Line 17, delete "Nos." and insert -- No. --

In Column 1, Line 17, delete "and EY027061"

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 3

<210> SEQ ID NO 1
<211> LENGTH: 419
<212> TYPE: PRT
<213> ORGANISM: Homo sapiens

```
<400> SEQUENCE: 1

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
                115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
                260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
        290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
                340                 345                 350

Leu Asn Pro Gly Lys Cys Ala Cys Glu Cys Thr Glu Ser Pro Gln Lys
                355                 360                 365

Cys Leu Leu Lys Gly Lys Lys Phe His His Gln Thr Cys Ser Cys Tyr
            370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
```

<210> SEQ ID NO 2
<211> LENGTH: 354
<212> TYPE: PRT
<213> ORGANISM: Homo sapiens

<400> SEQUENCE: 2

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Gly Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 3
<211> LENGTH: 555
<212> TYPE: PRT
<213> ORGANISM: Homo sapiens

<400> SEQUENCE: 3

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
```

-continued

```
                370                 375                 380
Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
                420                 425                 430

Pro Cys Ser Asn Met Leu Gly Met Leu Ser Gly Leu Ile Ala Asp Ser
                435                 440                 445

Gln Ile Ser Ala Ser Ser Thr Gln Glu Tyr Leu Trp Ser Pro Ser Ala
                450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
                500                 505                 510

Thr Ala Val Glu Ala Arg Ala Phe Val Arg Lys Phe Lys Val Ser Tyr
                515                 520                 525

Ser Leu Asn Gly Lys Asp Trp Glu Tyr Ile Gln Asp Pro Arg Thr Gln
                530                 535                 540

Gln Pro Lys Val Gly Cys Ser Trp Arg Pro Leu
545                 550                 555
```